(12) United States Patent
Stieber et al.

(10) Patent No.: US 8,894,644 B2
(45) Date of Patent: Nov. 25, 2014

(54) PLASMA DEVICE FOR SELECTIVE TREATMENT OF ELECTROPORED CELLS

(75) Inventors: Manfred Stieber, Greifswald (DE); Klaus-Dieter Weltmann, Ostseebad Binz (DE); Thomas Von Woedtke, Horst (DE); Christian Wilke, Greifswald (DE); Uwe Ehrenberg, Hanshagen (DE)

(73) Assignee: INP Greifswald Leibniz-Inst fuer Plasmaforschung, Greifswald (DE)

( * ) Notice: Subject to any disclaimer, the term of this patent is extended or adjusted under 35 U.S.C. 154(b) by 1065 days.

(21) Appl. No.: 12/855,177

(22) Filed: Aug. 12, 2010

(65) Prior Publication Data
US 2011/0112528 A1 May 12, 2011

Related U.S. Application Data

(63) Continuation of application No. PCT/EP2009/051650, filed on Feb. 12, 2009.

(30) Foreign Application Priority Data

Feb. 12, 2008 (DE) .......................... 10 2008 008 614

(51) Int. Cl.
| *A61B 18/12* | (2006.01) |
| *A61N 1/44* | (2006.01) |
| *A61L 2/00* | (2006.01) |
| *A61L 2/14* | (2006.01) |
| *A61N 1/04* | (2006.01) |
| *A61N 1/32* | (2006.01) |
| *C12N 13/00* | (2006.01) |
| *H05H 1/24* | (2006.01) |

(52) U.S. Cl.
CPC ................. *A61N 1/44* (2013.01); *A61L 2/0011* (2013.01); *A61L 2/14* (2013.01); *A61N 1/0412* (2013.01); *A61N 1/327* (2013.01); *C12N 13/00* (2013.01); *H05H 1/24* (2013.01)
USPC .................... 606/41; 606/1; 607/96; 128/898

(58) Field of Classification Search
USPC ............................................................ 606/1
See application file for complete search history.

(56) References Cited

U.S. PATENT DOCUMENTS

| 7,608,839 B2 | 10/2009 | Coulombe et al. |
| 2002/0122896 A1 | 9/2002 | Kim et al. |
| 2006/0148737 A1 | 7/2006 | Harmon |
| 2009/0004717 A1 | 1/2009 | Jaroszeski et al. |

FOREIGN PATENT DOCUMENTS

| DE | 60106901 T2 | 11/2005 |
| DE | 102006019664 A1 | 10/2007 |
| DE | 102007025452 A1 | 12/2008 |

OTHER PUBLICATIONS

U.S. Appl. No. 13/389,938, filed Jul. 19, 2012, Weltmann, et al.

*Primary Examiner* — Aaron Roane
(74) *Attorney, Agent, or Firm* — Oblon, Spivak, McClelland, Maier & Neustadt, L.L.P.

(57) ABSTRACT

A method and device for treatment of living cells with cold atmospheric pressure plasma while simultaneously applying selective electroporation of the cells are provided. The method is useful for the local selective killing of cancer cells, improvement of wound treatment and sterilization or decontamination of objects.

16 Claims, 4 Drawing Sheets

PLASMA DEVICE FOR SELECTIVE TREATMENT OF ELECTROPORED CELLS

CROSS REFERENCE TO RELATED APPLICATIONS

This application is a continuation application of International Application No. PCT/EP2009/051650, filed Feb. 12, 2009, the disclosure of which is incorporated herein by reference in its entirety. The parent application claims priority to German Application No. 10 2008 008 614.2, filed Feb. 12, 2008, the disclosure of which is incorporated herein by reference in its entirety.

BACKGROUND OF THE INVENTION

1. Field of the Invention

The invention relates to a method and devices for treatment of living cells with a cold atmospheric pressure plasma with simultaneous selective electroporation of the cells being treated. The invention provides for local, selective killing of cancer cells, for improvement of the treatment of wounds and for an improved antimicrobial plasma effect.

2. Description of the Related Art

1. Cancer Therapy:

The standard methods of cancer therapy used individually or in combination are currently surgery, chemotherapy and radiation therapy. A method known as "electroporation therapy" (EPT), "electrochemotherapy" (ECT) or "high-voltage impulse therapy" (HVIT) is now undergoing clinical trials. This method is based on the fact that the membrane pores of cancer cells can be selectively and reversibly opened for a short time by selective application of pulsed electric fields (electroporation), thus achieving significantly increased cell absorption of the active ingredients used for chemotherapy, such as bleomycin or cisplatin. The advantages compared with conventional chemotherapy include 1) the necessary dose of active ingredient can be reduced by a factor of approximately twenty with electrochemotherapy, and that, by virtue of the selective killing, a tissue-preserving effect with minimal scarring can be achieved, as can a large reduction of the side effects caused by the chemotherapeutic agent. Since the cancer cells differ from the healthy cells in terms of size, cell-membrane structure and electrical properties, selectivity of electroporation can be achieved by suitable choice of amplitude, number, duration and frequency of the high-voltage impulses. German patent documents DE 69604509, DE 69928383 and DE 60106901 describe various devices for achieving such controlled, selective electroporation of cells.

Even though the dose of active ingredient may be considerably reduced in electrochemotherapy, it is not possible to dispense completely with the use of expensive chemotherapeutic agents, which still have side effects for healthy body tissue, albeit to a lesser extent than in conventional chemotherapy.

2. Healing of Chronic Wounds:

Since chronic wounds are usually the consequence of basic diseases, the primary approach to curing them lies in diagnosis and causal therapy of the basic ailment. In many cases, however, curing of the basic disease is not possible, and so it is endeavored by diverse local therapeutic measures, such as surgical interventions, wound cleaning and disinfection, the use of antibiotics and of special wound dressings and bandages, to achieve healing of the wound despite persistence of the basic disease.

The constantly growing range of available therapeutic agents (salves, tinctures, powders, antiseptics, antibiotics) as well as bandage materials and systems of bandaging substances for treatment of chronic wounds, and the associated problem of the correct choice and application, may lead to a therapeutic procedure that is characterized by a large number of diverse, uncoordinated and often ineffective medical measures (poly-pragmatism) and may be the cause of healing delays and cost increases.

3. Sterilization, Decontamination and Processing of Medical Technical Products:

The use of the known standard methods for thermal, chemical, UV and gamma-ray sterilization may be no longer possible for a growing number of medical technical products, because of material-related, construction-specific as well as environmental and health concerns. Therefore, the development of methods for material-preserving and effective antimicrobial treatment is becoming increasingly important. Plasma-related methods may offer interesting possibilities for addressing this problem and intensive effort to the development of this technology is in progress throughout the world.

Pathogen kill rates on the order of the 6-log reduction necessary for sterilization and material-preserving decontamination of medical technical products of sensitive, thermally labile materials have been achieved employing plasma technology, although only for some relevant microorganisms. However, the potential utility of this technique has not been fully exhausted.

DETAILED DESCRIPTION OF THE INVENTION

Figure 1:
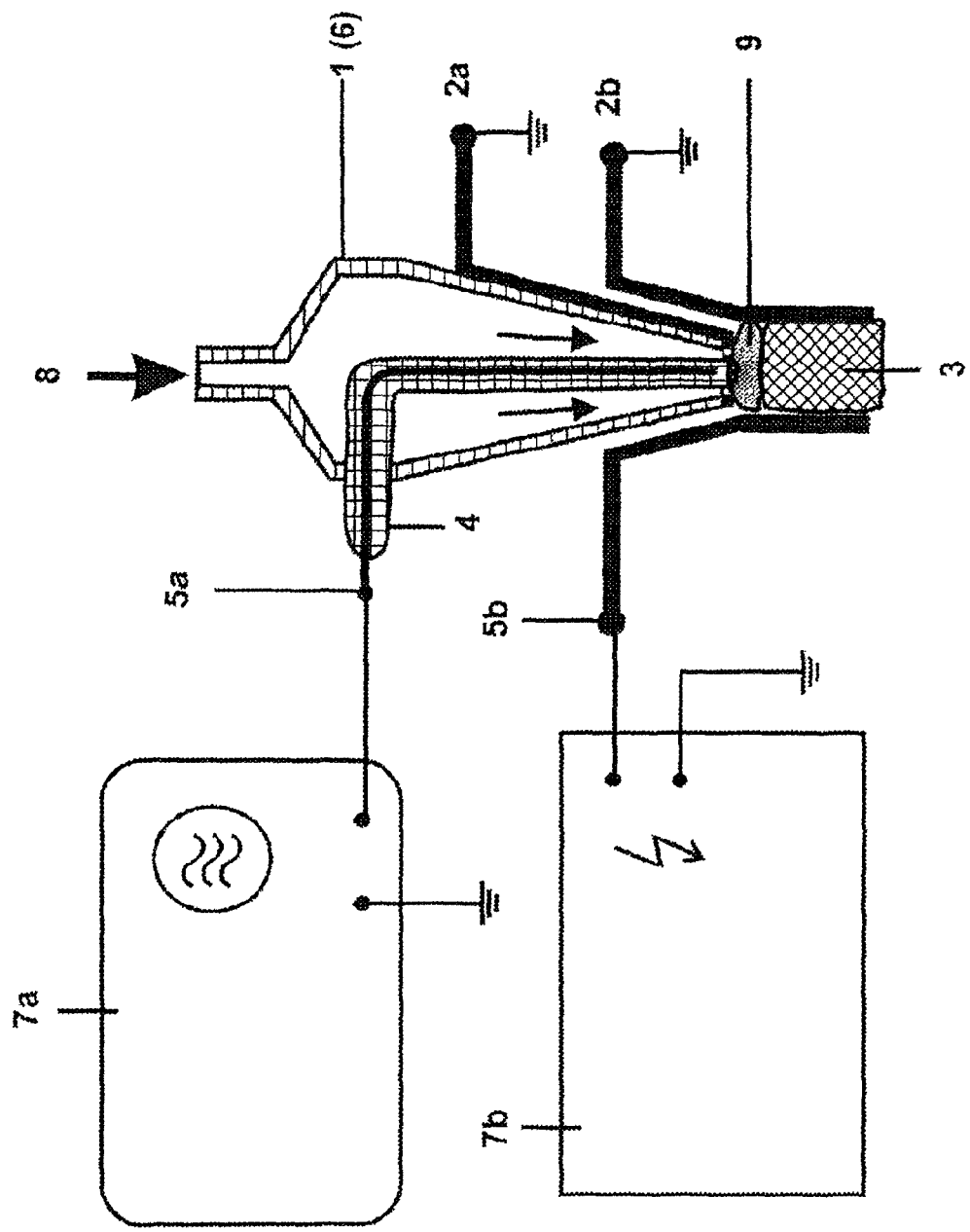
FIG. 1 shows a schematic diagram of one embodiment according to the invention having electroporation electrodes (2b and 5b) of plate design. Plasma treatment is by surface barrier discharge.

The object of the invention was to eliminate the disadvantages of conventionally known methods of sterilization and decontamination of objects. A further object was to provide a method for the treatment of cancer wherein conventional treatments such as chemotherapy or radiation are eliminated or reduced.

These and other objects have been achieved by the present invention, the first embodiment of which provides a device, comprising:

a means for generating a plasma; and a means for applying conventional electroporation;

wherein living cells are simultaneously treated with a plasma and electroporation.

In a further preferred embodiment the present invention provides a device for treatment of living cells simultaneously with a plasma and electrodeposition, comprising:

at least one plasma-source electrode;

at least one electroporation electrode;
a gas supply;
at least one voltage supply; and
an cell tissue position;
wherein the living cells to be treated are located in the object position,
the at least one electroporation electrode is located at the cell tissue position, and
the plasma generator provides a plasma to the object position.

In a second embodiment, the present invention provides a method for sterilization of objects, comprising:
subjecting cell membrane pores of microorganisms to be killed in the sterilization to reversible electroporation, thereby causing them to open temporarily; and
simultaneously exposing the opened cells to a plasma containing radicals;
wherein a more effective killing of the cells by the radicals generated in the plasma is obtained.

In a further preferred embodiment the present invention provides a method for treatment of an object, a wound or a portion of skin, comprising:
placing the object, wound or portion of skin in the cell tissue position of the treatment device;
generating a plasma comprising radicals;
applying pulsed electric fields to the object, wound or portion of skin; and
simultaneously treating the object, wound or portion of skin with the plasma;
wherein the treatment is biological decontamination or sterilization.

In another preferred embodiment, the present invention provides a method for treatment of skin cancer, comprising:
selectively opening the cancer cells of a diseased skin by impedance-controlled electroporation,
generating a plasma having radicals;
exposing the opened cancer cells to the plasma having radicals; and
killing the electropored cancer cells by the radicals generated in the atmospheric pressure plasma;
wherein the treatment does not comprise chemotherapeutic agents.

In a further preferred embodiment, the present invention provides a method for treatment of skin cancer, comprising:
selectively opening the membrane pores of cancer cells of a skin cancer area by impedance-controlled electroporation; and
treating the electropored cancer cells with an atmospheric pressure plasma containing radicals;
wherein the method comprises the treatment device,
the cancer cells are killed by the radicals generated in the atmospheric pressure plasma and
the treatment does not comprise chemotherapeutic agents.

The invention is based on the idea of increasing the efficacy of atmospheric pressure plasmas on living cells by simultaneously electroporing the cells. For example, during application for cancer therapy, the membrane pores of the cancer cells of a diseased skin area are selectively opened by impedance-controlled electroporation, so that the electropored cancer cells can be killed by the radicals generated in the atmospheric pressure plasma (such as a plasma jet or surface barrier discharge) and the additional use of chemotherapeutic agents can be dispensed with.

On the basis of this invention, it is possible to solve the following problems:
1. Problem of cancer therapy: local, selective killing of cancer cells without the use of chemotherapeutic agents, 2. Problem of healing of chronic wounds: new therapeutic approach to improvement of wound healing as a combination of an antiseptic effect with stimulation of new growth of healthy tissue, 3. Problem of sterilization, decontamination and processing of medical technical products: improved antimicrobial plasma effect by combination with electroporation of the microorganism cells.

In treatment of the cells of chronic wounds, parallel application of electroporation and atmospheric pressure plasma, employing selected optimized treatment parameters may provide a more effective antiseptic effect of the plasma and stimulation of new growth of the healthy tissue cells.

More effective sterilization may be obtained in the method of the present invention because the cell membrane pores of the microorganisms to be killed are temporarily opened by reversible electroporation with simultaneous plasma effect, thereby permitting more efficient destruction of the microorganism cells by the radicals generated in the plasma.

Application of plasma technology to cancer therapy, may provide a considerable savings in treatment costs by reduction or elimination in the use of expensive chemotherapeutic agents. Moreover, the treatment may be free of side effects.

The present invention may offer the advantage that a polypragmatic treatment is replaced by an efficient and cost-effective, universally applicable treatment, which may combine by an effective antiseptic effect with stimulation of new growth of healthy tissue.

A substantial improvement of sterilization efficiency may be obtained according to the invention by employing electroporation in combination with atmospheric pressure plasma during sterilization, decontamination or processing of medical technical products.

Figure 2:
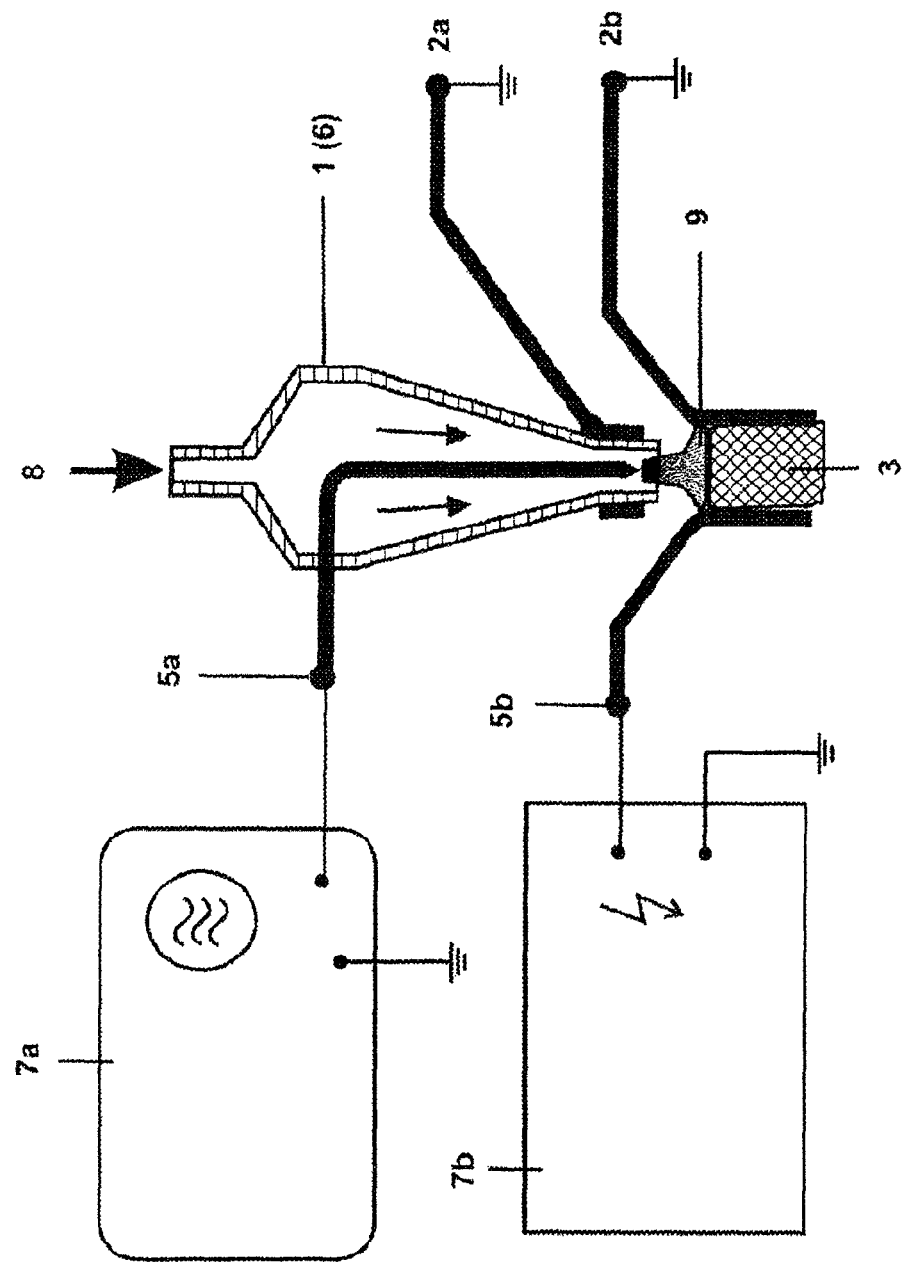
FIG. 2 shows a schematic diagram of one embodiment according to the invention having electroporation electrodes (2b and 5b) of plate design. Plasma treatment is by plasma jets.
Figure 3:
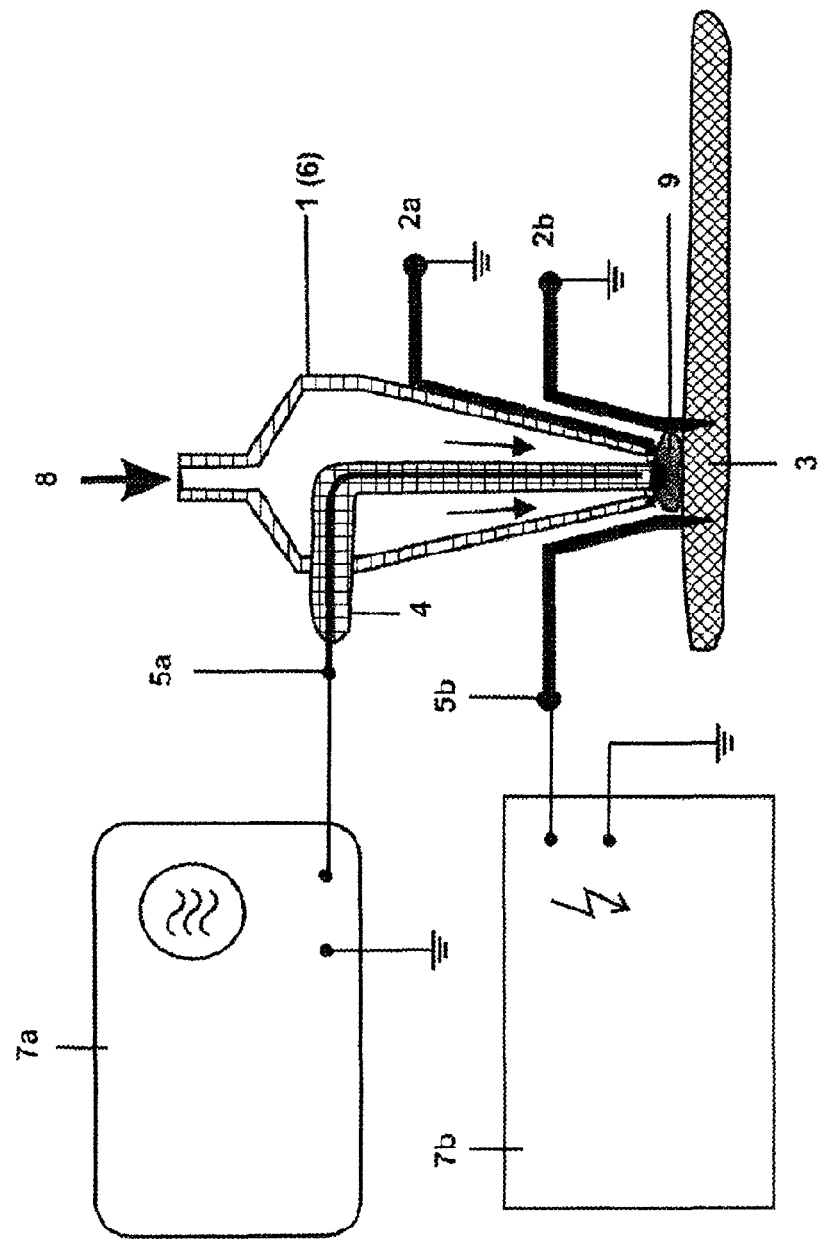
FIG. 3 shows schematic diagram of one embodiment according to the invention having electroporation electrodes of needle design. Plasma treatment is by surface barrier discharge.
Figure 4:
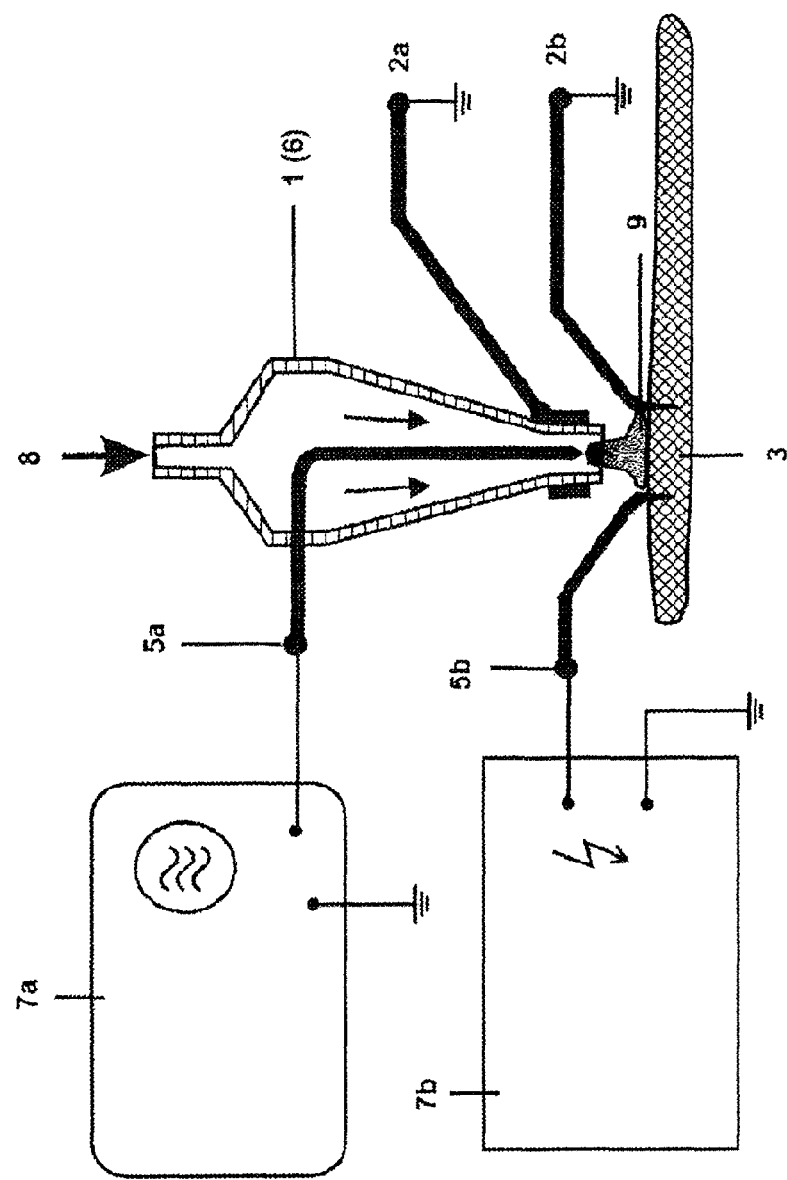
FIG. 4 shows schematic diagram of one embodiment according to the invention having electroporation electrodes of needle design. Plasma treatment is by plasma jets.

Having generally described this invention, a further understanding can be obtained by reference to certain specific examples of the claimed device as shown in FIGS. 1 to 4, which are provided herein for purposes of illustration only and are not intended to be limiting. The reference numbers of the Figs. are described as follows:

| List of reference numerals | | | |
|---|---|---|---|
| 1 | Gas nozzle | 2 | Grounded electrode |
| 2a | Grounded plasma-source electrode | 2b | Grounded electroporation electrode |
| 3 | Cell tissue position | 4 | Dielectric |
| 5 | High-voltage electrode | 5a | Plasma-source electrode |
| 5b | Electroporation electrode | 6 | Insulation |
| 7 | Voltage supply | 7a | Plasma-source voltage supply |
| 7b | Electroporation voltage supply | | |
| 8 | Gas supply | 9 | Plasma |

Numerous modifications and variations on the present invention are possible in light of the above teachings. It is therefore to be understood that within the scope of the appended claims, the invention can be practiced otherwise than as specifically described herein.

The invention claimed is:
1. A device, comprising:
at least one plasma-source electrode;
at least one electroporation electrode;
a gas supply;
at least one voltage supply; and
a cell tissue position;
an object position;
wherein said device is capable of exposing living cells to plasma and electroporation at the same time;

wherein the living cells to be treated are located in the cell tissue position, the at least one electroporation electrode is located at the object position, and the plasma generator provides a plasma to the object position.

2. The device according to claim 1, wherein the plasma generated is an atmospheric pressure plasma.

3. The device according to claim 2, wherein the atmospheric pressure plasma is a cold or non-thermal atmospheric pressure plasma.

4. The device according to claim 1, further comprising a gas nozzle, at least one dielectric, insulation and at least one high-voltage electrode.

5. A method for sterilization of objects, comprising:
   with the device according to claim 1,
      subjecting cell membrane pores of microorganisms to be killed in the sterilization to reversible electroporation, thereby causing them to open temporarily; and
      simultaneously exposing the opened cells to a plasma containing radicals;
   wherein a more effective killing of the cells by the radicals generated in the plasma is obtained by the exposure to plasma and electroporation at the same time compared to exposure to plasma alone.

6. A method for treatment of an object, a wound or a portion of skin, comprising:
   placing the object, wound or portion of skin in the cell tissue position of the device according to claim 1;
   generating a plasma comprising radicals;
   applying pulsed electric fields to the object, wound or portion of skin; and
   simultaneously treating the object, wound or portion of skin with the plasma;
   wherein the treatment is biological decontamination or sterilization.

7. A method for treatment of skin cancer, comprising:
   with the device according to claim 1,
      selectively opening the cancer cells of a diseased skin by impedance-controlled electroporation,
      generating a plasma having radicals;
      exposing the opened cancer cells to the plasma having radicals; and
      killing the electropored cancer cells by the radicals generated in the atmospheric pressure plasma;
   wherein the treatment does not comprise a chemotherapeutic agent.

8. The method according to claim 7, wherein the plasma is an atmospheric pressure plasma.

9. The method according to claim 8, wherein the atmospheric pressure plasma is a cold or non-thermal atmospheric pressure plasma.

10. A method for treatment of cancer, comprising:
    with the device according to claim 1,
       applying pulsed electric fields to cancer cells; and
       simultaneously treating the cancer cells with a plasma containing radicals.

11. The method according to claim 10, wherein the plasma is an atmospheric pressure plasma.

12. The method according to claim 11, wherein the atmospheric pressure plasma is a cold or non-thermal atmospheric pressure plasma.

13. The method according to claim 10, wherein the cancer cells are placed in the cell tissue position of the device.

14. A method for treatment of skin cancer, comprising:
    with the device according to claim 1,
       selectively opening the membrane pores of cancer cells of a skin cancer area by impedance-controlled electroporation; and
       treating the electropored cancer cells with an atmospheric pressure plasma containing radicals;
    wherein the cancer cells are killed by the radicals generated in the atmospheric pressure plasma; and
    wherein the treatment does not comprise a chemotherapeutic agent.

15. A method for treatment of chronic wounds, comprising:
    with the device according to claim 1,
       applying pulsed electric fields to cells of the chronic wound; and
       simultaneously applying an atmospheric pressure plasma containing radicals to the cells to which the pulsed electric fields are applied.

16. A method for sterilization of objects comprising a microorganism, comprising:
    with the device according to claim 1,
       selectively opening the membrane pores of cells of the microorganisms by impedance-controlled electroporation; and
       simultaneously treating the electropored microorganism cells with an atmospheric pressure plasma containing radicals;
    wherein the microorganism is killed by the radicals generated in the atmospheric pressure plasma.

* * * * *